May 18, 1965 J. H. CHAMPION Plant Pat. 2,516

BOUGAINVILLEA PLANT

Filed Sept. 26, 1963

INVENTOR:
JACK H. CHAMPION
BY
Rummler & Snow
ATT'YS

United States Patent Office

Plant Pat. 2,516
Patented May 18, 1965

2,516
BOUGAINVILLEA PLANT

Jack H. Champion, P.O. Box 35, Sanitarium, Calif.

Filed Sept. 26, 1963, Ser. No. 311,928
1 Claim. (Cl. Plt.—54)

This disclosure concerns a new and distinct variety of Bougainvillea plant discovered by me in 1958 as a sport of the unpatented variety "Mary Palmer," in cultivation at Poona, India. This sport was particularly distinguished by its large showy bracts of white, magenta-rose, and mixed white and magenta-rose colors all growing on the same bush, and because of this unusual, but very attractive feature I made cuttings of the new sport and propagated it asexually to fix the new variety and preserve its distinctive characteristics.

Asexual propagation of my new variety of Bougainvillea plant has been carried on in my growing grounds at Sanitarium, Napa County, California by means of cuttings, through several generations and its novel and distinctive characteristics have been found to be fully fixed and to hold true from generation to generation. The new variety is a persistent and prolific bloomer, blooming continuously from March to December, and longer in mild winters, in Northern California. The bracts of my new variety are slightly smaller in size than some other varieties of Bougainvillea, but the new plant has many more bracts in each cluster than ordinarily occur in other Bougainvillea varieties growing under similar conditions, and the primary distinction of my new variety resides in its consistent habit of producing branches having bracts of a rich magenta-rose color, others having bracts of white, and still others in which the bracts are of two colors, magenta-rose and white. These bracts appear in large clusters, some of one color and others of mixed colors in the same cluster, thus providing a decorative plant of outstanding beauty.

Figure 1:
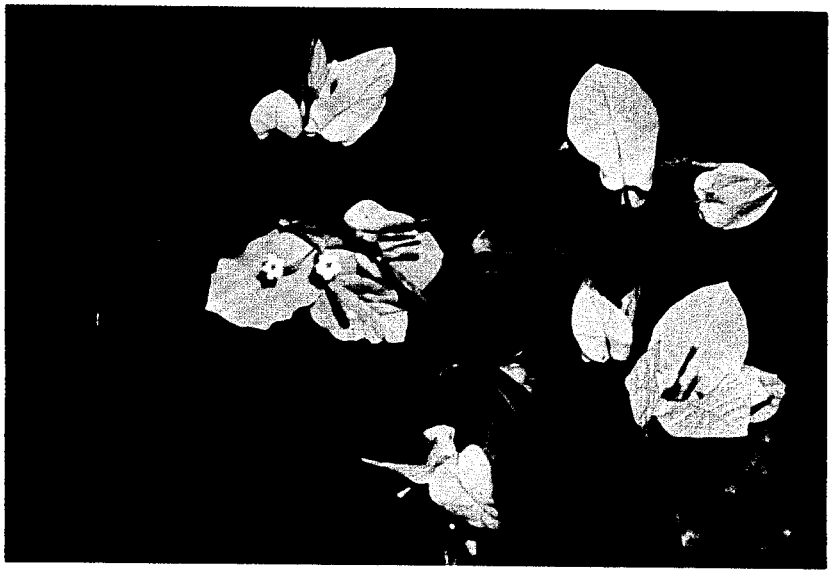
Figure 2:
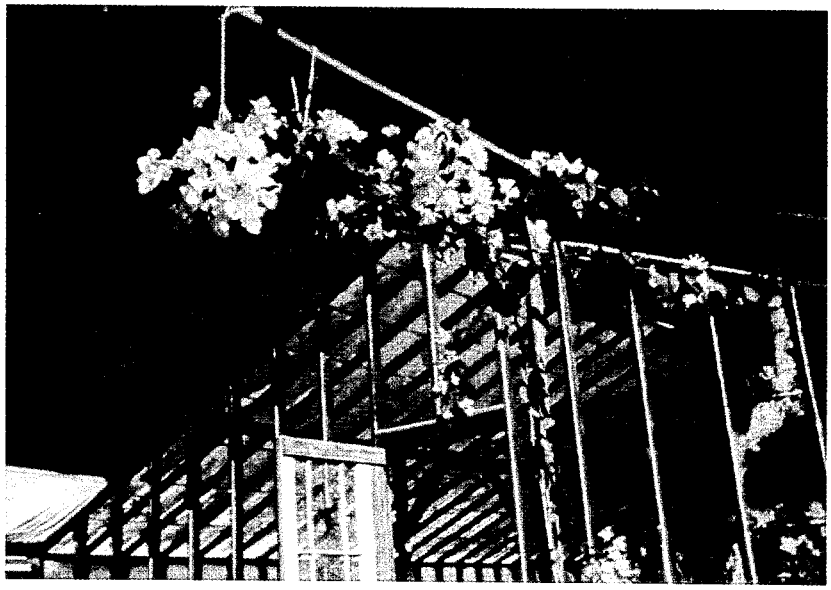

The accompanying color drawing shows the multi-color characteristic of my new variety of Bougainvillea plant, FIG. 1 showing a close-up view of the differently colored clusters of bracts growing on the same plant and FIG. 2 showing the plant growing on an arbor.

The following is a somewhat more detailed description of new new Bougainvillea variety:

*The plant*

Origin: Sport of Bougainvillea "Mary Palmer" (unpatented).

Botanic classification: *Bougainvillea glabra sanderiana* variety.

Form: Climbing bush.

Height: 15 feet or more.

Growth: Vigorous, strong and sturdy.

Foliage: Abundant.

*Size of leaf.*—3" x 4".

*Shape of leaf.*—Ovate with acuminate tip.

*Texture.*—Smooth.

*Color.*—Upper side—dark green. Under side—lighter green.

Plant has thorns of brown color when mature and about ½ inch to 1 inch long.

*The blooms*

The plant blooms continuously and profusely from March to December in California. In mild winters the plant will bloom for a longer period.

The flowers, which in size are similar to the common varieties of Bougainvillea, grow in clusters with each flower tube extending from a bract averaging about 2 inches long and 1½ inches wide. The flowers are 5 lobed and, in the new variety, the indentation at the tip of each lobe is deeper than that of other varieties. Also, the flower lobes are fuller in my new variety, which gives the flower a more ruffled effect.

The flower tubes in the solid magenta-rose bracts are also of a magenta-rose color. However, in the all-white bracts the flower tubes are of a light green color and in the bi-colored bracts the flower tubes are generally of the same light green color but often appear bi-colored, also.

Each plant of my new variety has three types of flower heads which occur in a more or less random fashion; i.e. heads of all magenta-rose bracts, heads of all white bracts, and heads having a combination of magenta-rose bracts and white bracts together with bracts that are part white and part magenta-rose.

Th bi-colored bracts always have the white at the base of the bract and the white extends various distances toward the tip end where the remainder of the bract area is of the magenta-rose color. Thus the bi-colored bracts have various proportions of the white and magenta-rose areas and serve to "tie together" the all-white and all-magenta-rose colored bracts appearing on the same plant to give a kaleidoscopic effect as the plant is stirred by the breezes.

The blooms are not affected by wet or hot weather and there is very little, if any, change in color in the bracts of magenta-rose as they age. Sometimes, some of the white bracts will take on a tinge of pink as they age but others will remain a substantially pure white. When growing in shade the magenta-rose bracts will have a deeper, more magenta, color and when growing in the sunlight the bracts will have a glowing rose color.

The blooms of this new variety have no fragrance but the bracts are very persistent and the lasting quality on the plant is excellent. The new variety appears to be a much more prolific and persistent bloomer, even in the early stages of growth, than any other Bougainvillea grown under similar conditions and with its multi-color blooming habit it provides a highly decorative plant of great beauty.

Having now described my new discovery, I claim:

A new and distinct variety of Bougainvillea plant, substantially as herein shown and described, characterized particularly as to novelty by its unique and consistent habit of growth, producing a combination of flowering heads having bracts of all white, all magenta-rose, and mixed white and magenta-rose color all growing at random on the same plant and at the same time.

No references cited.

ABRAHAM G. STONE, *Primary Examiner.*